(12) United States Patent
Manion

(10) Patent No.: US 6,919,374 B1
(45) Date of Patent: *Jul. 19, 2005

(54) VISCOSITY MODULATING SUBSTANCE AND USE THEREOF

(75) Inventor: Carl V. Manion, Oklahoma City, OK (US)

(73) Assignee: Oklahoma Medical Research Foundation, Oklahoma City, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 10/088,713

(22) PCT Filed: Sep. 21, 2000

(86) PCT No.: PCT/US00/25874

§ 371 (c)(1),
(2), (4) Date: Jul. 22, 2002

(87) PCT Pub. No.: WO01/22983

PCT Pub. Date: Apr. 5, 2001

Related U.S. Application Data

(60) Provisional application No. 60/156,119, filed on Sep. 25, 1999.

(51) Int. Cl.[7] .................. A61K 31/235; A61K 31/245; A61K 38/05; A61P 7/02; A61P 7/06

(52) U.S. Cl. .................. 514/533; 514/2; 514/19; 514/534; 514/538; 514/542; 514/814; 514/815; 514/822; 514/825

(58) Field of Search .................. 514/533, 814, 514/815, 825, 2, 19, 534, 538, 542, 822

(56) References Cited

U.S. PATENT DOCUMENTS

| 5,654,334 A | 8/1997 | Edmundson et al. ....... 514/538 |
| 6,384,076 B1 * | 5/2002 | Manion et al. ............ 514/542 |

FOREIGN PATENT DOCUMENTS

| WO | WO9700692 | 1/1997 | .......... A61K/38/05 |
| WO | 98/13062 | * 4/1998 | |
| WO | WO0018418 | 4/2000 | .......... A61K/38/00 |

OTHER PUBLICATIONS

MEDLINE Abstract, accession No. 95072271, available from Medline Jan. 1995.*
MEDLINE Abstract, accession No. 93088234, available from Medline Jan. 1993.*
MEDLINE Abstract, accession No. 90333175, available from Medline Sep. 1990.*
Edmundson, A.B. and Manion, C. V., 1998. "Treatment of osteoarthritis with aspartame," *Clinical Pharmacology and Therapeutics* 63:580–593.
Manion, C. V., et al., 1999. "Sickle Cell Disease and Aspartame," *Clinical Pharmacology & Therapeutics*, US, Mosby–Year Book, St. Louis, MO, vol. 65, p. 194, Feb. 1999, Abstract PIII–70.
Manion, C. V., et al. 2000. "Sickle Cell Viscosity Alteration With Aspartame," *Clinical Pharmacology & Therapeutics*, US, Mosby–Year Book, St. Louis, MO, vol. 67, p. 102, Feb. 2000, Abstract PI–54.
Pokrovskii, A. V., et al., 1979. "Hemo Rheological Disorders in Patients with Athero Sclerotic Lesion of the Abdominal Aorta and their Correction Using Aspirin," *Kardiologiya*, vol. 19, No. 2, 1979, pp. 54–61.
Rodgers, et al., 1987. "Pairings and polarities of the 14 strands in sickle cell hemoglobin fibers," *Proc Natl Acad Sci USA*, 84:6157–6161.

* cited by examiner

*Primary Examiner*—John Pak
(74) *Attorney, Agent, or Firm*—Eugenia S. Hansen; Conley Rose, P.C.

(57) ABSTRACT

It has now been found that N-L-alpha-aspartyl-L-phenylalanine 1-methyl ester (APM) lowers whole blood viscosity in patient, including those suffering from sickle cell disease and plasma cell dyscrasias. Upon in vivo APM treatment patients experienced a significant lowering of whole blood viscosity. In vitro addition of APM to patients samples having elevated whole blood viscosity resulted in reduced viscosity over time. These in vivo and in vivo results identify APM as a therapeutic agent for molecular diseases which lead to elevated whole blood viscosity. A method by which APM treatment can be monitored is also disclosed.

8 Claims, 3 Drawing Sheets

VISCOSITY MODULATING SUBSTANCE AND USE THEREOF

This application claims the benefit of Provisional application Ser. No. 60/156,119 filed on Sep. 25, 1999.

TECHNICAL FIELD OF INVENTION

The present invention relates to the viscosity modulating effects of N-L-alpha-aspartyl-L-phenylalanine 1-methyl ester, its use in pharmaceutical preparations for the treatment of diseases affected by blood viscosity, and a method of monitoring disease progression.

BACKGROUND OF THE INVENTION

In the body, whole blood viscosity increases as the blood flow through the capillaries decreases. Decreased blood flow can result from elevated levels of circulating blood cells, aggregation of blood cells, distortion of blood cell shape such as the sickling of red blood cells, elevated levels of circulating immunoglobulins, and gelation of certain types of immunoglobulins such as cryoglobulin. Numerous diseases are known to be associated with decreased blood flow leading to increased blood viscosity, and common symptoms include anemia, severe pain, and thrombotic complications.

Patients suffering from various plasma cell dyscrasias, for example, multiple myeloma, primary or Waldenstrom's macroglobulinemia, and certain heavy chain diseases which clinically mimic multiple myeloma routinely exhibit increased blood viscosity. These diseases are often associated with various dysproteinemias caused by overproduction of monoclonal immunoglobulins including markedly elevated plasma IgM concentrations and cryoglobulinemia. Systemic lupus erythematosus (lupus; SLE) and arthritis are also associated with similar dysproteinemias, and patients may exhibit increased whole blood viscosity.

Whole blood viscosity is often increased during complications in sickle cell disease. Under low oxygen tension, sickle cell deoxyhemoglobin (HbS) forms multi-stranded fibers (Rodgers, et al. 1987. *Proc Natl Acad Sci USA* 84:6157:6157–6161; Eaton, W. A. and Hofrichter, J. 1990. *Adv Protein Chem* 40:63–279) that force a red blood cell (RBC) into a crescent, or sickle, shape. Physiologically, decreased hemoglobin concentration associated with sickled RBCs impair blood flow, resulting increased whole blood viscosity.

Preventive treatment for these diseases is unknown, and therapy is symptomatic. Sickle cell and multiple myeloma patients are treated with hydration, analgesics for pain relief, and exchange transfusion for severe cases of anemia. Chemotherapy utilizing alkylating agents and corticosteroids is prescribed to multiple myeloma patients and macroglobulinernia patients. For hyperviscosity in macroglobulinemia patients, plasmapheresis is commonly practiced. Therapy for SLE and arthritis includes analgesics, arthralgias, and corticosteroids.

U.S. Pat. No. 5,654,334 discloses a method for decreasing pain comprising administering N-L-alpha-aspartyl-L-phenylalanine 1-methyl ester (APM) and certain derivatives having the following structure

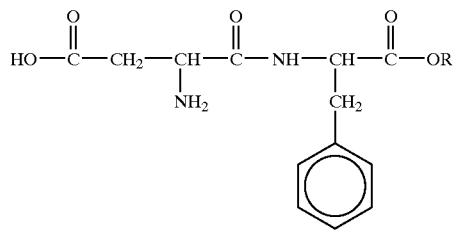

wherein R is H or an alkyl having 1–6 carbon atoms, as a pain reliever which is especially effective in relieving pain associated with osteoarthritis and multiple sclerosis. Further, International Application WO 97/00692 discloses a pharmaceutical preparation for administration to obtain an analgesic effect comprising APM derivatives wherein R is H or an alkyl containing 2 to 6 carbons as well as the antipyretic effect of APM and its derivatives. In a clinical trial, APM was demonstrated to alleviate the pain and inflammation of osteo- and mixed osteo- and rheumatoid arthritis by an unknown mechanism (Edmundson, A. B. and Manion, C. V. 1998. *Clinical Pharmacology and Therapeutics* 63:580–593).

International Application WO 00/18418 discloses a pharmaceutical preparation comprising APM or one of its derivatives wherein R is an alkyl useful in obtaining an antisickling effect in red blood cells. The application discloses that APM interacts with the HbS molecule to the extent that the stacking of the HbS molecules within the red blood cell is significantly altered, leading to a reduction in the capacity of red blood cells containing HbS to sickle with hypoxemia.

It has now been found that APM lowers whole blood viscosity in vivo, resulting in a viscosity modulating agent useful in the treatment of diseases of interest. A method of monitoring the progression of disease based on whole blood viscosity has also been found.

SUMMARY OF THE INVENTION

In one aspect, the present invention is use of the compound

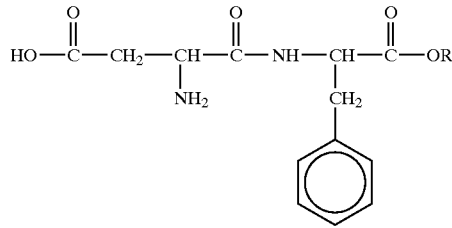

where R is $CH_3$ or an alkyl to prepare a pharmaceutical composition useful for effecting a. reduction in whole blood viscosity in a mammal. Preferably, the alkyl has 2 to 6 carbons.

In another aspect, the present invention is a pharmaceutical preparation in dosage unit form adapted for administration to obtain a reduction in whole blood viscosity, comprising, per dosage unit, an effective, nontoxic amount of a compound comprising

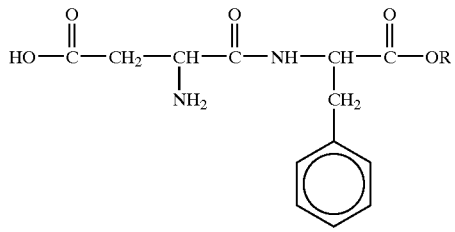

wherein R is $CH_3$ or an alkyl and a pharmaceutical carrier. Preferably, the alkyl has 2 to 6 carbons. A preferred dosage is from about 1 milligram to about 6 milligrams per kilogram body weight.

In another aspect, the present invention is a method for treatment of high whole blood viscosity in a patient comprising administering in a treatment regimen to said patient an effective amount of a composition comprising

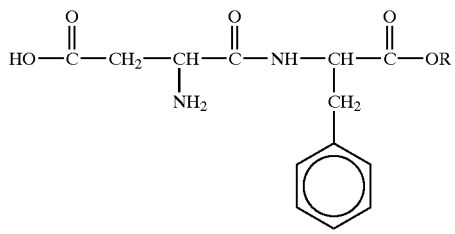

where R is $CH_3$ or an alkyl, wherein said treatment regimen is capable of reducing whole blood viscosity in the patient. Preferably, the alkyl has 2 to 6 carbons. A preferred effective amount is from about 1 milligram to about 6 milligrams per kilogram body weight.

In another aspect, the present invention is a method for reducing whole blood viscosity in a patient blood sample, comprising collecting a blood sample from the patient; and adding to the collected blood sample an effective amount of a composition comprising the compound

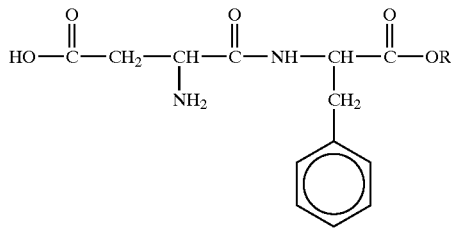

wherein R is $CH_3$ or an alkyl, wherein the effective amount causes a reduction in whole blood viscosity. Preferably, the alkyl has 2 to 6 carbons.

In another aspect, the present invention is a method for monitoring the reduction of whole blood viscosity in a patient receiving treatment with a composition comprising

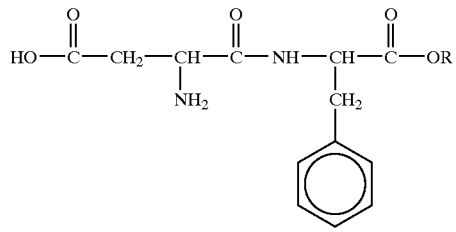

where R is $CH_3$ or an alkyl having 2 to 6 carbons comprising: (a) at a first time point, collecting a blood sample from the patient administration of the composition to form a first patient sample; (b) measuring the viscosity of the first patient sample to obtain a first viscosity value; (c) at a second time point, collecting a blood sample from the patient to form a second patient sample; (d) measuring the viscosity of the second patient sample to obtain a second viscosity value; and (e) comparing the second viscosity value to the first viscosity value, wherein a reduction of viscosity is demonstrated by the second viscosity value being less than the first viscosity value. In a preferred embodiment, the first and second viscosity values are determined by drawing an aliquot of each patient sample into a pipette which is in a stationary vertical position and measuring the time required to expel a drop of the patient sample from the pipette using constant pressure to obtain a time interval as the viscosity value.

In yet another aspect, the invention is a screening method for determining if a patient's whole blood viscosity can be reduced by a treatment regimen with a composition comprising

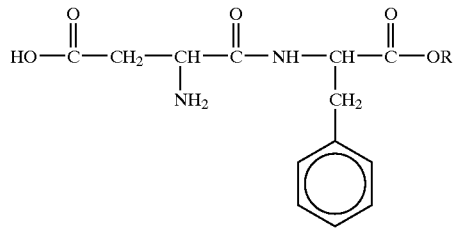

where R is $CH_3$ or an alkyl of 2 to 6 carbons, comprising (a) collecting a blood sample from the patient prior to administration of the composition to form an untreated patient sample; (b) measuring the viscosity of the untreated patient sample to obtain a baseline viscosity value; (c) administering to the patient the composition at an amount from about 1 milligram to about 6 milligrams per kilogram body weight; (d) after administrating the composition to the patient, collecting a blood sample from the patient to form a treated patient sample; and (e) measuring the viscosity of said treated patient sample to obtain a post-treatment viscosity value; and (f) comparing the post-treatment viscosity value to the baseline viscosity value, wherein the post-treatment viscosity value being less than the baseline viscosity value demonstrating the composition is capable of reducing whole blood viscosity in the patient and wherein the post-treatment viscosity value being greater than or equal to the baseline viscosity value demonstrating the composition is not capable of reducing whole blood viscosity in the patient. In a preferred embodiment, the first and second viscosity value are determined by drawing an aliquot of each patient sample into a pipette which is in a stationary vertical position and measuring the time required to expel a drop of the patient sample from the pipette using constant pressure to obtain a time interval as the viscosity value.

In yet another aspect, the invention is a method for treating a patient having a disease characterized by abnormally viscous whole blood comprising administering in a treatment regimen to the patient an effective amount of a composition comprising

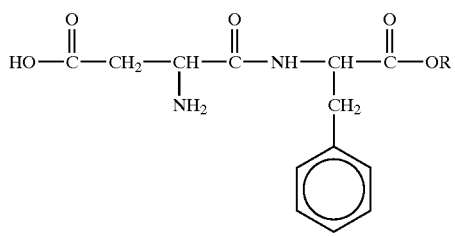

where R is $CH_3$ or an alkyl, wherein the treatment regimen is capable of reducing whole blood viscosity in the patient. Preferably, the alkyl has 2 to 6 carbons. A preferred effective amount is from about 1 milligram to about 6 milligrams per kilogram body weight.

DETAILED DESCRIPTION

Figure 1:
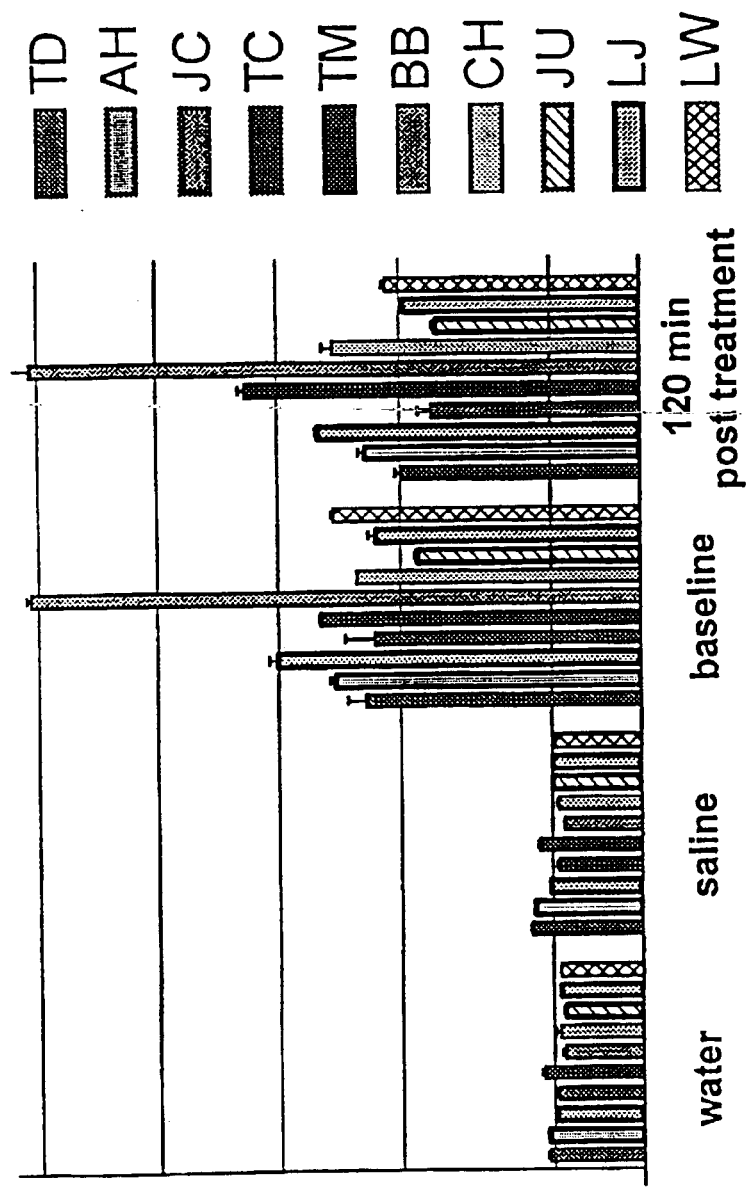
FIG. 1 is a graph depicting the viscosity measurements for each of the ten patient samples taken at baseline and 120 minutes post-APM administration. The first grouping is the concurrent measurement of the viscosity of water at the time and conditions under which the patient's blood sample was tested; the second grouping is the concurrent measurement of the viscosity of saline at the time and conditions under which the patient's blood sample was tested; the third grouping is the viscosity measurement for each patient taken at baseline (Time 0); and the fourth grouping is the viscosity measurement for each patient taken at 120 minutes post-treatment. In each grouping, the bars appear from left to right in the same order as the listings in the legend presented from top to bottom. The patients identified as TM, BB, and CH whose data is given in the respective 5th, 6th and 7th bar from the left in each treatment group had Hgbsc, or SC disease. The patient identified as TC whose data is given in the 4th bar from the left in each treatment group had sbthal disease. The other patients had sickle cell disease, or SS disease.

It has now been found that N-L-alpha-aspartyl-L-phenylalanine 1-methyl ester (APM) and certain derivatives having the structure of

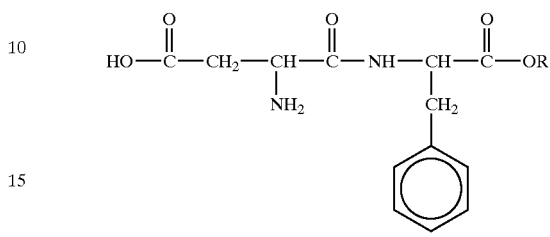

wherein R is $CH_3$ or an alkyl, preferably a alkyl of 2 to 6 carbons, lowers whole blood viscosity in vivo and in vitro, providing for the first time a means by which elevated blood viscosity can be altered. Upon treatment with an effective amount of APM, symptoms and the resultant risks associated with high whole blood viscosity are lessened for patients suffering from one of the diseases of interest.

It is to be understood that the term "APM" used herein refers to N-L-alpha-aspartyl-L-phenylalanine 1-methyl ester and/or one of its derivative having the structure given above wherein R is an alkyl. An effective amount of APM which can effect a reduction in whole blood viscosity is from about 1 milligram to about 6 milligrams per kilogram body weight. A preferred range is from about 3 milligrams to about 6 milligrams per kilogram body weight. Most preferred is about 6 milligrams per kilogram body weight. The dosage can be repeated over time for continued relief, preferably at 6 milligrams per kilogram body weight every 12 hours.

APM can be administered orally, parenterally, intraperitoneally, or sublingually. It can be administered via ingestion of a food substance containing APM in a volume sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid; corn starch; a lubricant such as magnesium stearate; a glidant such as colloidal silicon dioxide; and additional sweetening and flavoring agents. When a capsule form is used the liquid carrier such as a fatty oil may be used. Capsules and tablets can be coated with sugar, shellac and other enteric agents as is known. APM can also be in a controlled-release formulation or by any controlled-release mechanical means known in the art.

With the exception of patients suffering from phenylketonuria, APM is considered as a GRAS (generally regarded as safe) substance. APM is commercially available, e.g., as ASPARTAME™ (G.D. Searle & Company, Chicago, Ill.). Its preparation is also disclosed in U.S. Pat. No. 3,492,131. While APM is preferred, it is believed that derivatives of APM can also be used as viscosity modulating agents. Exemplary derivatives include but are not limited to the ethyl, propyl and butyl esters, and the derivatives should maintain the sweetening property of the dipeptide. Such derivatives, which can be determined using the monitoring methods provided in the examples below, are considered to fall within the scope of this invention.

An in vitro method has also been found by which the effectiveness of APM treatment for lowering blood viscosity can be monitored. The method presented in Example 1 uses blood samples taken from patients suffering from sickle cell disorders. The same method would be utilized for blood samples from other diseases of interest. It is to be understood that the examples below are representative of the invention and are intended to be illustrative of the invention, but are not to be construed to limit the scope Of the invention in any way. Modifications may be made in the structural features of the invention without departing from the scope of the invention. It will be readily apparent to those skilled in the art that alternative materials methods may also be utilized without departing from the scope of the invention. In particular, the method for measuring viscosity of the whole blood presented in Example I is merely representative and any method known in the art for measuring the viscosity of whole blood can be used in the present invention.

EXAMPLE 1

Viscosity Screening Method for APM Efficacy in Sickle Cell Patients

The efficacy of APM treatment can be monitored by measuring the viscosity of patient blood samples before and after treatment. Normal blood viscosity increases with increasing hemoglobin concentration. While patients with sickle cell disease are anemic, the viscosity of their blood appears in the abnormal range, and the viscosity increases with an increase in the number of sickle cells relative to the number of normal cells as the anemia is corrected.

Blood samples were obtained from ten patients having homozygous HgBss disease or heterozygous Hgbsc disease before and after a blinded administration of APM at 1.5 (low dose), 3 (medium dose), or 6 (high dose) milligrams per kilogram body weight. Table I gives the patients' characteristics.

TABLE 1

Patient Characteristics

| No. | Age | Sex | Disease[a] | Hgb | Hct | Dose[b] |
|---|---|---|---|---|---|---|
| TD | 13 | M | ss | 7.6 | 25.4 | H |
| AH | 11 | F | ss | 8.1 | 23.3 | M |
| JC | 13 | M | sbthal | 7.5 | 25.1 | L |
| TC | 9 | F | sbthal | 7.9 | 25.6 | H |
| JU | 4 | M | ss | 7.9 | 22.6 | M |
| LJ | 4 | M | ss | 7.9 | 22.6 | H |
| TM | 19 | F | sc | 10.3 | 30.2 | L |
| BB | 39 | F | sc | 11.5 | 39.0 | H |
| CH | 52 | F | sc | 8.0 | 26.0 | M |
| LW | 3 | F | ss | 7.4 | 24.0 | M |
|  | 16.7 | 3M/5F | ss5/sc3 | 8.52 | 26.64 |  |

[a]ss homozygous HgBss; sc = heterozygous HbS and HbC; sbthal = homozygous HbS with -thalassemia.
[b]H = high dose, 6 mg/kg body weight; M = medium dose, 3 mg/kg body weight; L = low dose, 1.5 mg/kg body weight.

For comparative purposes, the number of sickle cells relative to the number of normal cells was obtained at 0, 30, 60, 120, 240, 480, and 1440 minutes after administration of APM according to the method given in Example 2.

Viscosity determinations using the RBC pipette method of Wright and Jenkins (1970, *Blood* 36:516) were made on each blinded whole blood sample before and 120 minutes after blinded administration of APM. Each measurement was made in triplicate. Control viscosity measurements using saline and water for each patient and normal whole blood were also made to validate the viscosity measurements.

To measure viscosity, 1.01 cc of the test fluid, i.e., either water, saline or blood, was drawn into an RBC pipette using a 50 cc syringe attached via rubber tubing to the top of the RBC pipette. Using a constant pressure of 20 mm by maintaining the pressure with visual feedback and hand pressure, the amount of time it took for the test fluid to drip out of the RBC pipette was measured with a stopwatch. Each measurement was made in triplicate. Changes in viscosity from baseline for patient blood samples were recorded and compared to normal controls.

The results of the study obtained by this viscosity monitoring method comparing viscosity measurements obtained at baseline and 120 minutes post-treatment are given in FIG. 1 and summarized in Table II. Of the five patients identified as HgBss (homozygous for HbS), blood viscosity decreased after treatment over time. For the two patients diagnosed as sbthal (homozygous HbS with β-thalassemia chain), blood viscosity also decreased after treatment over time, resembling the results obtained with HgBss. In contrast, blood samples taken from three patients diagnosed as Hgbsc (heterozygous HbS and HbC) showed increased viscosity after treatment over time. According to this data, this method of monitoring can be used to delineate "sickle cell disease" from certain "sickle cell trait" disorders, e.g., Hgbsc. The viscosity data was also compared against Pirofsky's change in viscosity vs. hematocrit standard, and the results were that the viscosity decreased in blood samples from patients with sickle cell disease (HgBss) and increased in blood samples from patients with sickle cell trait (Hbgsc).

TABLE II

Viscosity Results

| No. of Patients | Viscosity change | HgBss | sbthal | Hgbsc |
|---|---|---|---|---|
| 7 | decreasing | 5 | 2 |  |
| 3 | increasing |  |  | 3 |

Figure 2:
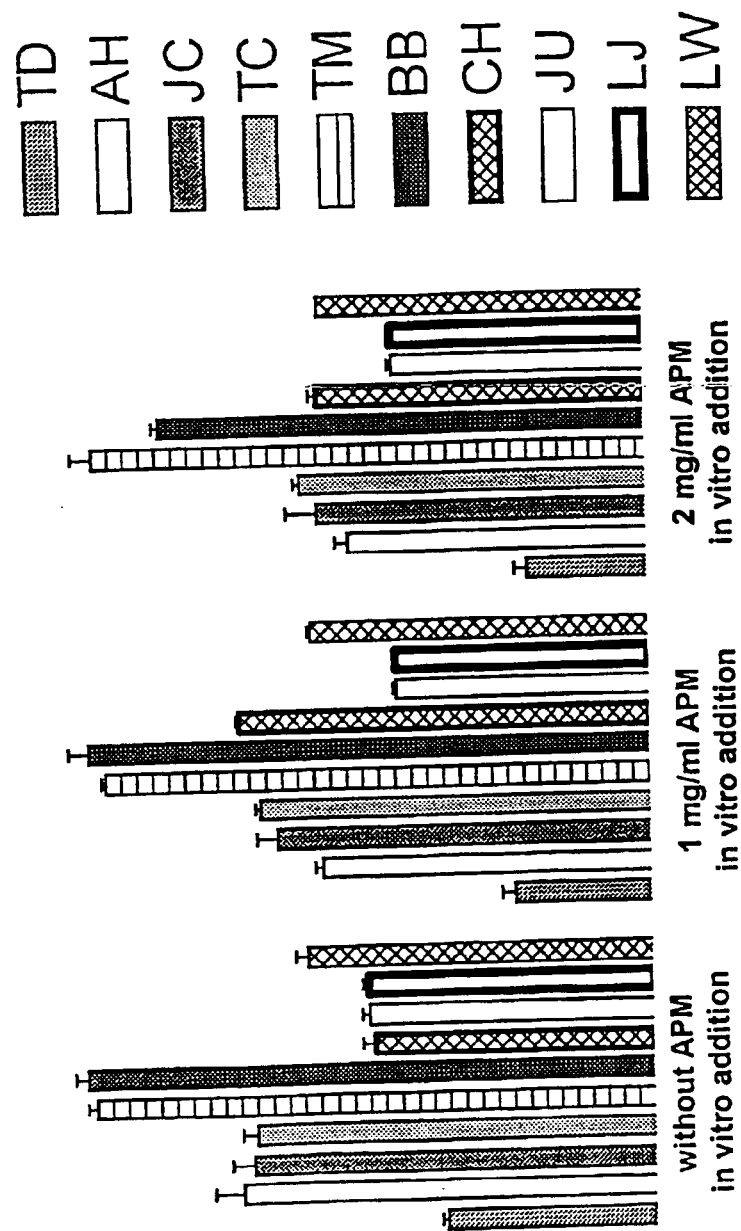
FIG. 2 is a graph depicting the viscosity measurements for each of the ten patient samples taken at 480 minutes post-in vivo APM treatment after the in vitro addition of 0, 1 milligram, or 2 milligrams of APM per milliliter. The first grouping was viscosity readings for patient samples measured at 480 minutes post-treatment to which no in vitro addition of APM was made; the second grouping was viscosity readings for patient samples measured at 480 minutes post-treatment to which 1 milligram per milliliter APM was added in vitro; and the third grouping was viscosity readings for patient samples measured at 480 minutes post-treatment to which 2 milligram per milliliter APM was added in vitro. In the grouping, the bars appear from left to right in the same order as the listings in the legend presented from top to bottom. The patients identified as TM, BB, and CH whose data is given in the respective 5th, 6th and 7th bar from the left in each treatment group had Hgbsc, or SC disease. The patient identified as TC whose data is given in the 4th bar from the left in each treatment group had sbthal disease. The other patients had sickle cell disease, or SS disease.

Samples with high viscosity readings at 480 minutes or 1,440 minutes post-treatment, chosen to represent patients with a validated response to APM who were returning to normal, were divided and treated with an additional 0, 1, or 2 milligrams/milliliter APM in vitro, in an effort to measure whether a second inducible sickling response was possible and if a second response to the in vitro APM addition could be observed. The viscosity of each sample at 480 minutes post-treatment was measured. As presented in FIG. 2, the viscosity of the blood samples from the patients classified as HgBss decreased over time when compared to the control. In contrast, blood samples from the Hgbsc patients showed an increase in viscosity over time compared to the control.

Figure 3:
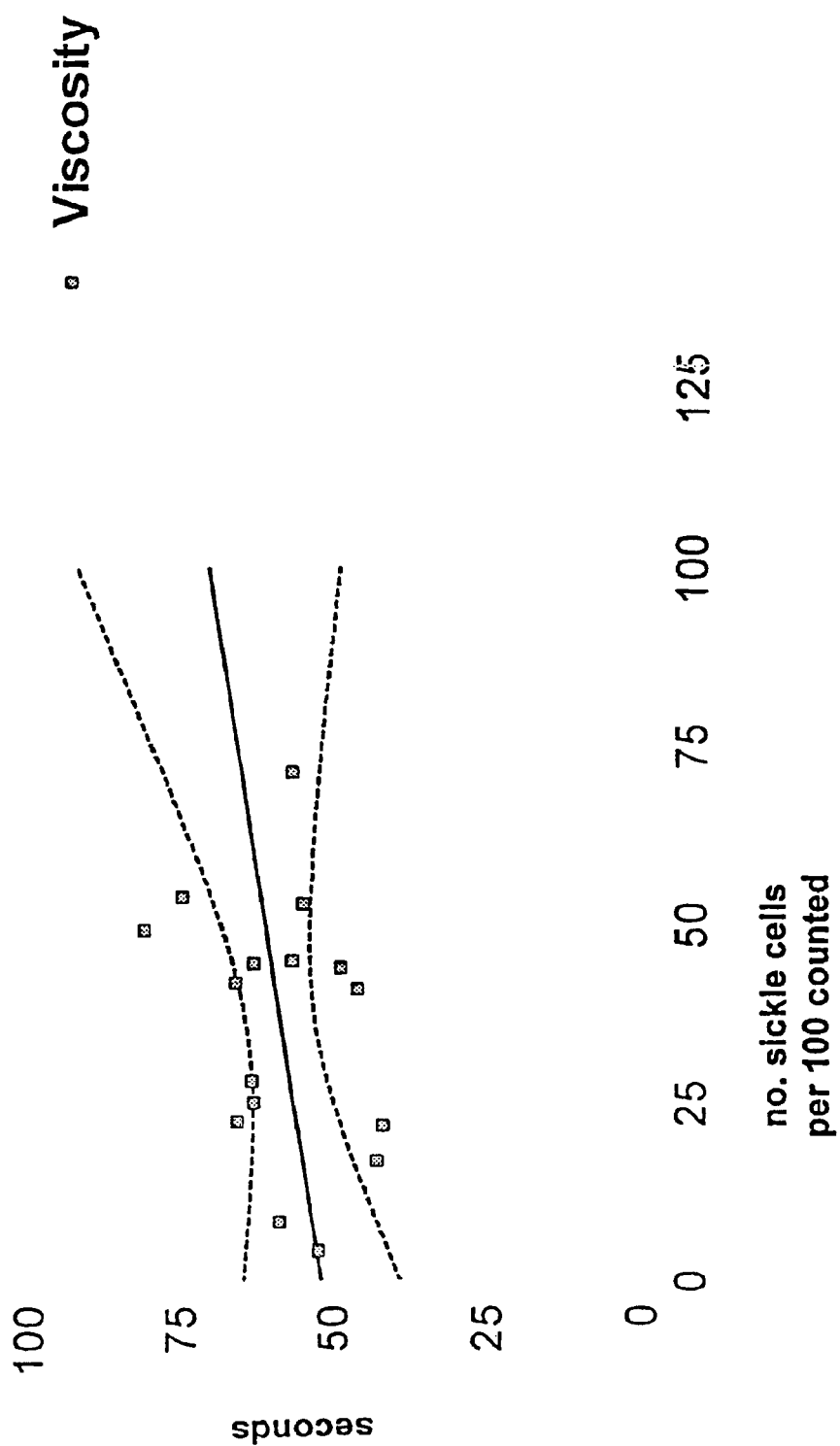
FIG. 3 is a graph depicting the correlation of sickle cell count to viscosity, demonstrating a linearly proportional correlation, i.e., as the number of sickle cells per total number of cells counted increases, viscosity also increases.

Baseline and 120 minute post-treatment viscosity measurements were compared with the number of sickle cells relative to the number of normal cells for correlation. The results as presented in FIG. 3 demonstrate that as the number of sickle cells relative to the number of normal cells increased, the blood viscosity also increased in an essentially linearly proportional correlation.

In summary, APM given orally reduces the number of sickle cells in HgBss blood and also reduces the viscosity of HgBss blood. The addition of APM in vitro also reduces the number of sickle cells in HgBss blood and the viscosity of HgBss blood. The Hgbsc blood was not affected by APM in vivo or in vitro.

The method disclosed herein was effective in providing a means whereby changes in viscosity were determinable for both in vivo and in vitro APM treatment. By measuring changes in viscosity of a patient sample upon in vitro addition of APM, this method can be applied to screen patients to determine their susceptibility to effective APM treatment in vivo. Once on APM treatment, the method can be applied to monitoring changes in viscosity as an indicator of the patient's response to therapy.

EXAMPLE 2

Metabisulfite Slide Test to Measure Sickling in Blood Samples In Vitro

Using the sickling test described herein, the number of sickle cells relative to the number of normal cells can be measured with and without APM treatment.

Blood was drawn before and 120 minutes after treatment with 0, 1.5, 3, or 6 milligrams APM per kilogram body weight in a blinded fashion from the ten patients into heparin tubes, stored in a refrigerator at approximately 10° C. and routinely tested within 36 hours of collection.

Normal blood devoid of abnormal hemoglobin was used as a control. For each heparinized patient blood sample and the normal blood control, experimental samples were prepared containing 0.25 milliliters of normal saline and 0.25 milliliters of blood.

Using metabisulfite to reduce HbS to the deoxy form (Daland, G. A. and Castle, W. B. 1948. *J Lab Clin Med* 33:1082–1088; Nelson, D. A. In Todd-Sanford-Davidsohn *Clinical Diagnosis by Laboratory Methods*, J. B. Henry, ed. (W.B. Saunders Co., Philadelphia, 1979, vol. 1, p. 1020), a baseline sickling test was run on each experimental sample. The sickling inducing agent was prepared fresh daily as follows: 10 milligrams metabisulfite in 1 milliliter isotonic saline. Multiple test slides were prepared for each experimental sample by adding approximately 300 microliters of the metabisulfite inducing agent to 50 microliters of well mixed blood and placing about 4 drops of the experimental sample onto the surface of a glass slide, placing a coverslip over the sample, and sealing the coverslip with a petroleum jelly bead to prevent oxygen from entering the sample. Triplicate counts were made manually of the number of sickle cells and normal cells, and the results were recorded as the number of sickle cells per 100 cells counted. Photomicrographs were also taken with a phase contrast microscope at 400 magnification, and the results were obtained from the photomicrographs as the number of sickle cells per 100 cells counted using a ScanPro scanner and software (Sigmascan, Jandel Scientific, San Rafael, Calif.). The manual counts correlated well with the scanned counts.

To account for natural or non-induced sickling of the experimental samples, a baseline sickling count was obtained for each heparinized patient blood sample and the normal blood control. Slides were prepared by adding 3 drops saline and 1 drop of the experimental sample onto the surface of a glass slide, placing a coverslip over the sample, and sealing the coverslip with a petroleum jelly bead to prevent oxygen from entering the sample. Photomicrographs were taken with a phase contrast microscope at 400 magnification, and the results were obtained from the photomicrographs as the number of sickle cells per 100 cells counted. This number of sickle cells per 100 cells counted was considered the baseline sickling count and was subtracted from the cell counts obtained with the metabisulfite induced samples.

After baseline counts were made, all experimental and control samples were stored in a refrigerator at 10° C. between each time point. Metabisulfite slides were subsequently prepared as given above at 30, 60, 120, 240, 480, and 1,440 minutes post administration, and the results were recorded as the number of sickle cells per 100 cells counted.

EXAMPLE 3

Method of Monitoring Therapy in a Multiple Myeloma Patient

The following method can be used for monitoring the reduction in whole blood viscosity in a patient suffering from multiple myeloma and exhibiting elevated whole blood viscosity upon administration of a composition comprising N-L-alpha-aspartyl-L-phenylalanine 1-methyl ester (APM). A blood sample from the patient is collected prior to treatment with APM. Saline, water, and normal whole blood is used as controls, and viscosity measurements are taken for saline, water, normal whole blood, and the patient blood with and without APM. To perform each viscosity measurement, an aliquot of the test fluid, i.e., water, saline, normal whole blood, or untreated patient blood is drawn into a pipette held stationary in a vertical position, and the time required to expel a drop of the test fluid from the lower end of the pipette is measured, providing a baseline time interval which serves as an indicator of blood viscosity. Preferably, a constant pressure of about 20 mm is applied to the upper end of the pipette at the time the measurement is taken. After administration of APM to the patient, a second blood sample is collected from the patient. Saline, water, and normal whole blood is used as controls, and viscosity measurements are taken for saline, water, normal whole blood, and the patient blood with and without APM. To perform each viscosity measurement, an aliquot of the test fluid, i.e., water, saline, normal whole blood, or untreated patient blood is drawn into a pipette held stationary in a vertical position, and the time required to expel a drop of the test fluid from the lower end of the pipette is measured, providing a post-treatment time interval which serves as an indicator of blood viscosity. Preferably, a constant pressure of about 20 mm is applied to the upper end of the pipette at the time the measurement is taken. The post-treatment time interval is then compared to the baseline time interval, and a reduction of whole blood viscosity is demonstrated when the post-treatment time interval is less than the baseline time interval.

I claim:

1. A method for treatment of high whole blood viscosity in a patient comprising administering in a treatment regimen to said patient an effective amount of a composition comprising

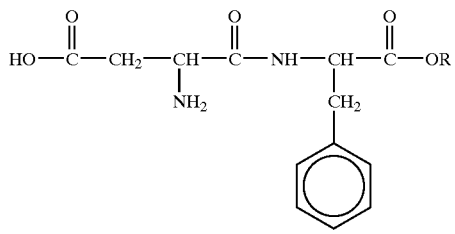

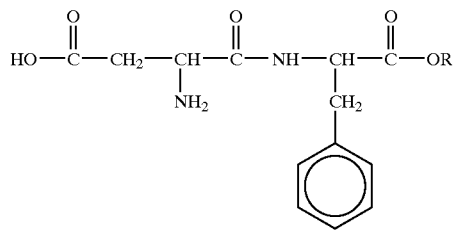

where R is $CH_3$ or an alkyl, wherein said effective amount causes a reduction in whole blood viscosity in said patient.

2. The method of claim 1, wherein said alkyl having 2 to 6 carbons.

3. The method of claim 1, wherein said effective amount is from about 1 milligram to about 6 milligrams per kilogram body weight.

4. The method of claim 2, wherein said effective amount is from about 1 milligram to about 6 milligrams per kilogram body weight.

5. A method for treating a patient having a disease characterized by abnormally viscous whole blood comprising administering in a treatment regimen to said patient an effective amount of a composition comprising where R is $CH_3$ or an alkyl, wherein said effective amount causes a reduction in whole blood viscosity in said patient.

6. The method of claim 5, wherein said alkyl having 2 to 6 carbons.

7. The method of claim 5, wherein said effective amount is from about 1 milligram to about 6 milligrams per kilogram body weight.

8. The method of claim 6, wherein said effective amount is from about 1 milligram to about 6 milligrams per kilogram body weight.

* * * * *

UNITED STATES PATENT AND TRADEMARK OFFICE
CERTIFICATE OF CORRECTION

PATENT NO.    : 6,919,374 B1
DATED         : July 19, 2005
INVENTOR(S)   : Carl V. Manion It is certified that error appears in the above-identified patent and that said Letters Patent is hereby corrected as shown below:

Title page,
Item [57], ABSTRACT,
Line 3, replace "patient" with -- patients --.

Column 1,
Line 31, replace "Waldenstrom's" with -- Waldenström's --.
Line 46, replace "84:6157:6157-6161;" with -- 84:6157-6161; --.
Lines 58 and 59, replace "macroglobulinernia" with -- macroglobulinemia --.

Column 7,
Line 13, replace "Of" with -- of --.

Signed and Sealed this

Eighteenth Day of October, 2005

JON W. DUDAS
*Director of the United States Patent and Trademark Office*